United States Patent [19]

Kondo et al.

[11] Patent Number: 4,626,392

[45] Date of Patent: Dec. 2, 1986

[54] PROCESS FOR PRODUCING CERAMIC BODY FOR SURGICAL IMPLANTATION

[75] Inventors: Kazuo Kondo; Masahiko Okuyama; Masakazu Watanabe; Satoshi Iio, all of Aichi, Japan

[73] Assignee: NGK Spark Plug Co., Ltd., Aichi, Japan

[21] Appl. No.: 716,437

[22] Filed: Mar. 27, 1985

[30] Foreign Application Priority Data

Mar. 28, 1984 [JP] Japan ................... 59-60046
Mar. 28, 1984 [JP] Japan ................... 59-60047

[51] Int. Cl.$^4$ ............... C04B 37/00; C04B 35/00; C04B 35/48
[52] U.S. Cl. ................... 264/62; 264/60; 264/66; 501/1; 501/103; 501/104; 501/153; 623/16
[58] Field of Search ............... 501/104, 1, 103; 264/60, 62, 43, 131, 66; 428/307.7; 623/16, 16 D, 16 G; 106/35

[56] References Cited

U.S. PATENT DOCUMENTS

| | | | |
|---|---|---|---|
| 4,308,064 | 12/1981 | Takami et al. | 501/135 |
| 4,376,168 | 3/1983 | Takani et al. | 501/1 |
| 4,525,464 | 6/1985 | Claussen et al. | 501/103 |
| 4,560,666 | 12/1985 | Yoshida et al. | 501/5 |

FOREIGN PATENT DOCUMENTS

| | | | |
|---|---|---|---|
| 2601550 | 7/1977 | Fed. Rep. of Germany | 264/62 |
| 2378733 | 9/1978 | France | 623/16 G |
| 53-118411 | 10/1978 | Japan | 501/104 |
| 58-126649 | 1/1983 | Japan | 623/16 D |

*Primary Examiner*—William R. Dixon, Jr.
*Assistant Examiner*—Kathleen E. Crotty
*Attorney, Agent, or Firm*—Sughrue, Mion, Zinn, Macpeak & Seas

[57] ABSTRACT

A process for producing a ceramic body suitable for surgical implantation that has high strength and toughness and good compatibility with bone material. A porous material is provided by semi-sintering a ceramic compact. The pores in the surface of the porous material are filled with a first powder of either tricalcium phosphate or apatite or both, or with a material of the fine powder and a powder of a material substantially the same as the material of the ceramic compact. The porous material is then fired at the sintering temperature of the ceramic compact. Following sintering, the surface of the porous material is coated with a fine apatite powder or a finally pulverized mixture of apatite and a calcium phosphate base frit. The resulting assembly is then fired at a temperature up to about 1,350° C.

4 Claims, No Drawings

PROCESS FOR PRODUCING CERAMIC BODY FOR SURGICAL IMPLANTATION

BACKGROUND OF THE INVENTION

The present invention relates to a process for producing a ceramic body for surgical implantation that has high strength and toughness, as well as good compatibility with bones.

A conventional process that is gaining an increasing interest in the art of producing ceramic bodies for surgical implantation consists of coating a high-strength ceramic material with another ceramic layer having good compatibility with bones. Among typical substrate materials are dental ceramics, polycrystalline alumina, and single-crystal alumina. Apatite is commonly used as the coating material. Japanese Unexamined Published Patent Application No. 118411/1978 entitled (in translation) "Apatite Coating Ceramics and Process for Producing the Same" discloses a method wherein an apatite powder is applied to the surface of a sintered substrate made of one of the materials listed above, followed by sintering the assembly.

Partially stabilized zirconia sintered body has recently drawn the interest of researchers because of its high strength and toughness. However, if this sintered body is coated with an apatite powder and sintered at 1,300° C., which is the usual sintering temperature for apatite, the resulting apatite coat adheres so weakly to the substrate that the former is easily rubbed off with finger pressure. Satisfactorily strong adhesion is not obtained even if the sintering temperature is increased to approximately 1,500° C. On the other hand, if the sintering temperature is elevated to about 1,600° C., the strength of the substrate made of partially stabilized zirconia sintered body is significantly reduced.

Most of the partially stabilized zirconia ceramics have sintering temperatures between 1,500° and 1,600° C., which are considerably higher than the sintering temperature of apatite (1,300° C.). Due to this factor, strong adhesion is unobtainable between a zirconia ceramic substrate and apatite layer. Additionally, if zirconia ceramics are subjected to another heating cycle at elevated temperatures, excessive growth of crystal grains coupled with a change in volume due to phase transformation induces cracking, which leads to a significant drop in the strength of the final product. Because of these unique characteristics of the partially stabilized zirconia ceramics as compared with the other conventional dental ceramics and alumina ceramics, it has been difficult to achieve strong adhesion by coating apatite powder to the zirconia ceramics surfaces.

SUMMARY OF THE INVENTION

The present invention has been accomplished in order to solve the problems mentioned above. According to one aspect of the invention, there is provided a process for producing a ceramic body for surgical implantation that comprises providing a porous material by semi-sintering a ceramic compact, filling the pores in the surface of the porous material with a powder of either tricalcium phosphate or apatite or both or with a mixture of the first powder and a powder of a material which is substantially the same as the ceramic compact, firing the porous material at the sintering temperature of the ceramic compact, coating the surface of the fired porous material with a fine apatite powder or a finely pulverized mixture of apatite and a calcium phosphate base frit, and sintering the assembly at a temperature up to 1,350° C. According to another aspect of the present invention, there is provided a process for producing a ceramic body for surgical implantation that comprises providing a porous material by semi-sintering a ceramic compact, impregnating the pores in the surface of the porous material with a mixture consisting of a calcium ion containing solution and a phosphate ion containing solution, firing the porous material at the sintering temperature of the ceramic compact, coating the surface of the fired porous material with a fine apatite powder or a finely pulverized mixture of apatite and a calcium phosphate base frit, and sintering the assembly at a temperature up to 1,350° C.

DESCRIPTION OF THE PREFERRED EMBODIMENTS

The porous material that is prepared by semi-sintering a ceramic compact in the first step of the process in accordance with the first aspect of the present invention provides the substrate for the ceramic body for surgical implantation that is obtained as the final product of the process of the present invention. This porous material has a porosity of 10 to 40% and is obtained from a ceramic compact which is capable of being sintered to a dense product having a porosity of several percent or less by firing such compact at a temperature which is about 200° to 400° C. lower than its sintering temperature.

The pores in the surface of this porous material are filled with a powder of either tricalcium phosphate or apatite or both or with a mixture of the first powder and a powder made of a material which is substantially the same as the ceramic compact. The so-treated porous material is densified by firing at the sintering temperature of the ceramic compact. The resulting sintered body has on its surface not only the substrate material but also the phosphate salt that easily adheres to the apatite. Therefore, the surface of the sintered body can be coated with a fine powder of apatite or a finely pulverized mixture of apatite and a calcium phosphate base frit by any known technique such as spreading, immersion or spraying, and a coat of the apatite or a mixture thereof with a frit that firmly adheres to the substrate can be obtained by sintering at low temperatures up to 1,350° C. without causing decomposition of the apatite.

The porous material that is prepared by semi-sintering a ceramic compact in the first step of the process according with the second aspect of the present invention also provides a substrate for a ceramic body for implantation that is obtained as the final product in the present invention. This porous material is an aggregate of primary particles that are obtained from a ceramic compact, which is capable of being sintered to a dense product with a porosity of not more than a few percent, by firing at a temperature which is about 200° to 400° C. lower than the sintering temperature of the shaped ceramic body. In this porous material, the primary particles are bound to one another to such an extent that the porous material retains a sufficient number of pores to enable a solution containing calcium or phosphate ions to penetrate into the compact while retaining structural integrity, even if the porous material is submerged in this solution. This porous material is immersed in a calcium ion containing solution to incorporate the same within the pores in the porous material. The thus-treated porous material is then dried. Subsequently, the porous material is immersed in a phosphate ion containing solution and dried. Thereafter, the treated porous material is densified by firing at the sintering temperature of the ceramic compact.

Since both the calcium ion containing solution and the phosphate ion containing solution have penetrated into the pores in the surface of the porous material, the dense compact of the porous material has on its surface not only the substrate material but also the calcium compound or phosphate salt that easily adheres to the apatite. Therefore, the surface of the sintered body can be coated with a fine powder of apatite or a finely pulverized mixture of apatite and a calcium phosphate base frit by any desired technique such as spreading, immersion or spraying, and a coat of the apatite or its mixture with the frit that firmly adheres to the substrate can be obtained by firing at low temperatures up to 1,350° C. without causing the decomposition of the apatite. Additionally, since the porous material of which the substrate is made has been densified by firing at its sintering temperature, the substrate has high mechanical strength. If the porous material contains partially stabilized zirconia as its principal component, the substrate has not only high mechanical strength but also enhanced toughness. The order in which the porous material is impregnated with the calcium ion containing solution and the phosphate ion containing solution is not critical to the purpose of the present invention and equally good results are obtained if the porous material is impregnated with the phosphate ion containing solution prior to the calcium ion containing solution, or even if the two solutions are impregnated in the porous material simultaneously.

The following examples are provided as further illustrations of the inventive process, but are not to be constructed as limiting.

EXAMPLE 1

An aqueous solution of zirconium oxychloride was mixed with an aqueous solution of yttrium chloride to form a co-precipitate, which was calcined at 800° C. to produce a powder of 97 mol% $ZrO_2$ and 3 mol% $Y_2O_3$. The powder was wet mixed with a water-soluble binder, and the mixture was spray dried. The spray dried powder was compacted with a rubber press at 1,500 kg/cm². The compact was degreased and subsequently maintained in the atmosphere at 1,200° C. for one hour to provide a porous material. The porous material was submerged in a 5% aqueous suspension of tricalcium phosphate and defoamed in vacuum for 5 minutes. After defoaming, the porous material was removed from the aqueous suspension, dried and sintered in the atmosphere at 1,550° C. for one hour so as to provide a sintered body. Five parts by weight of CaO-$P_2O_5$ frit (Ca/P atomic ratio=0.5), 95 parts by weight of apatite, and 1 part by weight of methyl cellulose were wet mixed to form a slurry. The slurry was spread onto the surface of the previously prepared sintered body, which was then sintered in the atmosphere at 1,300° C. for one hour, thereby producing a ceramic body suitable for surgical implantation. The peeling strength within the ceramic body and the apatite coat was checked by scratching the surface of the sample with a metal pin. No separation of the apatite coat occurred, suggesting strong adhesion to the substrate. The bending strength of the sample was about 80 kg/mm².

EXAMPLE 2

97 wt% of an $Al_2O_3$ powder (average particle size =1.5 microns), 2 wt% of a CaO powder, and 1 wt% of an MgO powder were wet mixed, and the mixture was spray dried. The spray dried powder was compacted in a mold at 800 kg/cm². After degreasing, the compact was maintained in the atmosphere at 1,150° C. for one hour to produce a porous material. A 30% aqueous suspension of a powder mixture of 5 parts by weight of apatite and 8 parts by weight of Al(OH)₃ was spread onto the porous material, which was subsequently sintered in the atmosphere at 1,600° C. for 1 hour. One hundred parts by weight of an apatite powder and one part by weight of methyl cellulose were wet mixed to form a slurry, which was spread onto the surface of the previously prepared sintered body, which was then sintered in the atmosphere at 1,300° C. for one hour, thereby producing a ceramic body suitable for surgical implantation. The peeling strength within the ceramic body and the apatite coat was checked by scratching the sample with a metal pin. No separation of the apatite coat occurred, suggesting strong adhesion to the substrate. The bending strength of the sample was about 40 kg/mm².

EXAMPLE 3

An aqueous solution of zirconium oxychloride was mixed with an aqueous solution of yttrium chloride to form a co-precipitate, which was calcined at 800° C. to produce a powder of 97 mol% $ZrO_2$ and 3 mol% $Y_2O_3$. The powder was wet mixed with a water-soluble binder, and the mixture was spray dried. The spray dried powder was compacted with a rubber press at 1,500 kg/cm². The compact was degreased and subsequently maintained in the atmosphere at 1,200° C. for one hour to provide a porous material. The porous material was submerged in an aqueous saturated solution of calcium hydroxide and defoamed in vacuum for 10 minutes. The defoamed porous material was removed from the aqueous suspension and dried. The dried material was then submerged in a 1% aqueous solution of orthophosphoric acid and subsequently defoamed and dried in the same manner as shown above. The so-treated porous material was fired in the atmosphere at 1,550° C. for one hour to provide a sintered body. The surface of this sintered body was spread with a separately prepared aqueous suspension of finely pulverized apatite. The sintered body was then fired at 1,300° C. for one hour so as to provide a ceramic body for implantation. The peeling strength within the ceramic body and the apatite coat was checked by scratching the surface of the sample with a metal pin. No separation of the apatite coat occurred, suggesting its strong adhesion to the substrate. The bending strength of the sample was about 70 kg/mm².

EXAMPLE 4

A ceramic body for surgical implantation was produced as in Example 1 except for the following points: 99 mol% of an $Al_2O_3$ powder (average particle size: 1.5 microns) was wet mixed with 1 mol% of an MgO powder; the granules were compacted in a mold at 800 kg/cm²; after degreasing the compact was maintained in the atmosphere at 1,200° C. for one hour to provide a porous material; and the porous material was sintered at 1,630° C. for 2 hours. The sample was checked for peeling strength as in Example 1, and no separation of the apatite coat occurred, suggesting strong adhesion to the substrate. The bending strength of the sample was about 40 kg/mm$^2$.

We claim:

1. A process for producing a ceramic body for surgical implantation, comprising the steps of: providing a porous material by semi-sintering a ceramic compact of a ceramic material having a sintering temperature higher than the sintering temperature of apatite; filling pores in the surface of said porous material with a powder selected from the group consisting of a fine powder of at least one of tricalcium phosphate and apatite, and a mixture of said fine powder and a powder of said ceramic material; firing said porous material at the sintering temperature of said ceramic compact; coating the surface of said fired porous material with a material selected from the group consisting of (1) a fine apatite powder and (2) a finely pulverized mixture of apatite and a calcium phosphate base frit; and sintering the ceramic body at a temperature up to 1,350° C.

2. The process according to claim 1, wherein said ceramic compact is made of a partially stabilized zirconia ceramic material.

3. A process for producing a ceramic body for surgical implantation, comprising the steps of: providing a porous material by semi-sintering a ceramic compact of a ceramic material having a sintering temperature higher than the sintering temperature of apatite; impregnating the pores in the surface of the porous material with a calcium ion containing solution and a phosphate ion containing solution; firing said porous material at the sintering temperature of said ceramic compact; coating the surface of said first porous material with a material selected from the group consisting of (1) a fine apatite powder and (2) a finely divided mixture of apatite and a calcium phosphate base frit; and sintering the ceramic body at a temperature up to 1,350° C.

4. The process according to claim 3, wherein said ceramic compact is made of a partially stabilized zirconia ceramic material.